United States Patent [19]

Hutton et al.

[11] 4,105,684
[45] Aug. 8, 1978

[54] PROCESS FOR THE PREPARATION OF ORGANOTIN TRIHALIDES

[75] Inventors: Ronald E. Hutton, Southport; Vincent Oakes, St. Helens; Joseph Burley, New Brighton, all of England

[73] Assignee: Akzo N.V., Arnhem, Netherlands

[21] Appl. No.: 793,363

[22] Filed: May 3, 1977

Related U.S. Application Data

[62] Division of Ser. No. 613,434, Sep. 15, 1975.

[30] Foreign Application Priority Data

Sep. 16, 1974 [NL] Netherlands .......................... 7412230

[51] Int. Cl.² ................................................ C07F 7/22
[52] U.S. Cl. .................................................. 260/429.7
[58] Field of Search ..................................... 260/429.7

[56] References Cited

U.S. PATENT DOCUMENTS

| 2,731,482 | 1/1956 | Stefl .................................... 260/429.7 |
| 3,607,893 | 9/1971 | Reifenberg et al. ............... 260/429.7 |
| 3,657,294 | 4/1972 | Gloskey ............................. 260/429.7 |
| 3,705,919 | 12/1972 | Heck ............................. 260/429.7 X |

OTHER PUBLICATIONS

Kagaku (Kyoto) 26,137 14 141 (1971).
J. Organometallic Chem. 25, 101–109 (1970).
Sawyer, Organolin Compounds, Marcel Dekkr, Inc. N.y.vol 2, pp. 261, 374, 375, 410, 411 (1971).

*Primary Examiner*—Helen M. S. Sneed
*Attorney, Agent, or Firm*—Stevens, Davis, Miller & Mosher

[57] ABSTRACT

Organotin trihalides are prepared by reacting in a polar solvent a stannous halide, hydrogen halide and an olefin of the formula

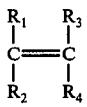

where $R_1$, $R_2$, $R_3$, and $R_4$ are an alkyl group, an oxygen-containing hydrocarbon group or a hydrogen atom and at least one of the groups contains a carbonyl group adjacent to the carbon-carbon double bond. The resulting product may be converted into organotin stabilizers for polyvinyl chloride and other polymers.

5 Claims, No Drawings

PROCESS FOR THE PREPARATION OF ORGANOTIN TRIHALIDES

This is a Division of application Ser. No. 613,434 filed Sept. 15, 1975.

This invention relates to the preparation of certain new organotin trihalides, which are particularly useful for conversion into organotin stabilizers for polyvinyl chloride or other polymers. In the synthesis of organotin compounds the formation of a tin-carbon bond constitutes a necessary step. A known method of forming such a bond is the Grignard route by the reaction $$SnCl_4 + 4RMgCl \rightarrow R_4Sn + 4 MgCl_2$$

where R = alkyl or substituted alkyl.

A different method is the aluminum alkyl route by the reaction $$3\ SnCl_4 + 4\ R_3Al \rightarrow 3\ R_4Sn + 4\ AlCl_3.$$

A third method is the Wurtz route:

$$SnCl_4 + 4\ RCl + 8\ Na \rightarrow R_4Sn + 8\ NaCl.$$

In these methods the $R_4Sn$ obtained may serve as a starting material for the preparation of $RSnHal_3$, $R_2SnHal_2$ and $R_3SnHaL$, where Hal represents a halogen atom. Although the above reactions are practically quantitative, the methods are unattractive because of the hazard they present to those who are to carry them out. Moreover, unlike the preparation of alkyl organotin compounds, the preparation by these routes of functionally substituted organotin compounds is not simple.

An alternative, less hazardous route, such as the direct preparation by the reaction $$Sn + 2RHal \rightarrow R_2SnHal_2$$

gives low yields with the formation of by-products such as $SnHal_2$, $R_3SnHal$ and $RSnHal_3$.

The insertion of stannous halides into a carbon-halogen bond in accordance with the reaction $$SnHal_2 + RHal \rightarrow RSnHal_3$$

requires the use of a catalyst and high temperatures, and gives poor yields.

The addition of an organotin hydride to an unsaturated hydrocarbon in accordance with the equation:

$$R_2SnH_2 + 2\ R'—CH = CH_2 \rightarrow R_2Sn(CH_2—CH_2—R')_2$$

must merely be considered an academic method in that the preparation of the organotin hydride in itself is both expensive and hazardous.

It is an object of this invention to provide a commercially attractive, non-hazardous process for the preparation of functionally substituted organotin trihalides.

The objects of the invention are accomplished by providing a process wherein the following materials are brought into reaction with each other in a polar solvent:
 (a) stannous halide
 (b) hydrogen halide and
 (c) an olefin of the formula

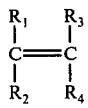

with 1-18 carbon atoms where $R_1$, $R_2$, $R_3$, and $R_4$ represent an alkyl group, an oxygen-containing hydrocarbon group or a hydrogen atom, provided that at least one of these groups contains a carbonyl group adjacent to the carbon-carbon double bond, after which the reaction product with the formula

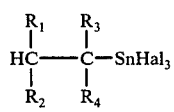

is isolated from the medium.

Generally, the halide may be chloride, bromide, iodide or even fluoride, although for reasons of cost and optimum yield chloride is usually preferred.

In order to have the reaction between the olefin and the other reactants proceed, it is considered essential that the olefin be activated, that is at least one of $R_1$, $R_2$, $R_3$ or $R_4$ contains an activating carbonyl radical adjacent to the olefinic double bond. The activating carbonyl radical may be an acid group, an ester group, an aldehyde group, an acid halide, or a ketone group.

Examples of olefins suitable to be used in the process according to the invention are:

| | |
|---|---|
| methyl acrylate | $CH_2{=}CH{-}\overset{\underset{\|}{O}}{C}{-}OCH_3$ |
| acrylic acid | $CH_2{=}CH{-}COOH$ |
| methyl crotonate | $CH_3{-}CH{=}CH{-}\overset{\underset{\|}{O}}{C}{-}OCH_3$ |
| mesityl oxide | $(CH_3)_2{-}C{=}CH{-}\overset{\underset{\|}{O}}{C}{-}CH_3$ |
| acryloyl chloride | $CH_2{=}CH{-}\overset{\underset{\|}{O}}{C}{-}Cl$ |
| methyl vinyl ketone | $CH_2{=}CH{-}\overset{\underset{\|}{O}}{C}{-}CH_3$ | and the like.

The starting materials react with each other at ambient temperature (10°-30° C.) to form the desired compound in a polar solvent, which is preferably an alkyl ether such as a diethyl ether. For olefins with one activating group and having no further substituents the reaction is almost quantitiative.

For example, the use of methyl acrylate with stannous chloride and hydrogen chloride results in a 98% yield, based on tin, of the desired organotin compound:

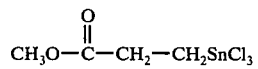

The new organotin compounds prepared according to the invention may be converted into very useful organotin stabilizers for polyvinyl chloride and other polymers by any of the established techniques for stabilizer preparation. Such preparation usually involves reaction with organic fatty acids having 6 to 18 carbon atoms, partial esters of maleic acid, alkyl thiols or mercapto-esters.

Accordingly, new organotin salts are thus obtained having the general formula R Sn $X_3$ with R denoting the organic group of the starting trihalide compound and X being the organic acid residue resulting from subject reaction with the acid or mercaptan.

Specifically, the organic residue X is selected from the group consisting of $-S(CH_2)_n COO$ alkyl with $n = 1$ or 2, $-$ S alkyl, $-$ OCO alkyl and $-$ OCOCH $=$ CHCOO alkyl.

The organotin trihalides prepared according to the invention have a certain stabilizing effect themselves on polymers and may also find utility as catalysts in the preparation of polyurethane foam and silicone resins or in esterification reactions.

However, their main utility is presently to be found as intermediates in the preparation of new organotin salts of the formula R Sn $X_3$ identified above.

These new salts make excellent components of stabilizer compositions for polymers, especially polyvinyl chloride. Their stabilizing performance is fully comparable to, if not better than, that of the conventional butyltin compounds.

Also their toxicity is generally lower, while the sulphur containing salts are often less noticeable in odor.

The following examples serve to illustrate the invention.

EXAMPLE 1

To a 500 ml, 3 neck flask fitted with a stirrer, thermometer, reflux condenser and gas inlet tube and placed in an ice/salt cooling bath were charged 80 g of anhydrous stannous chloride, 36.3 of methyl acrylate and 150 ml of dimethoxyethane as polar solvent. To the stirred solution were added 36 g of gaseous hydrogen chloride over a period of 2 hours, the temperature being maintained at 20° C. After this time the solvent was removed on a flash evaporator and the residue was extracted with 100 ml of toluene. The extract obtained was distilled off in vacuo at 100° C. and 4 mm Hg pressure to leave 117 g of a pale residue which crystallized on cooling. By elemental analysis and infrared spectroscopy it was found that a product of the composition

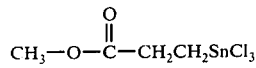

melting point 70° C., boiling point 174° C. (4 mm Hg) had been obtained in 89% yield, based on tin.

EXAMPLE 2

In the same apparatus as used in Example 1 and in accordance with the same procedure 70 g of anhydrous $SnCl_2$, 37.9 g of ethyl acrylate and 30 g of gaseous hydrogen chloride (added over a period of 1½ hours) were brought into reaction in 140 ml of diethyl ether, the temperature being kept at 15°-20° C. The solvent was removed on a rotary evaporator and the residue was extracted with 100 ml of toluene. From the extract the toluene and other volatile material were removed by distillation at up to 100° C./4 mm Hg pressure. The residue (95 grams) crystallized upon cooling and was found mainly to consists of

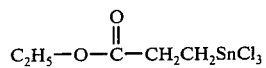

melting point 68° C. The yield was 79%, based on tin.

EXAMPLES 3-7

These examples concern similar preparations carried out by the same method and with the equipment described in Example 1, starting from different olefins and using other solvents.

The results are summarized in Table A.

Table A

| Example | olefin | product | melting point | yield |
|---|---|---|---|---|
| 3 | methyl methacrylate | $CH_3-O-\overset{\overset{O}{\|\|}}{C}-\overset{\overset{CH_3}{\|}}{CH}-CH_2SnCl_3$ | 86° C | 62 % |
| 4 | methyl crotonate | $CH_3-O-\overset{\overset{O}{\|\|}}{C}-CH_2-\overset{\overset{CH_3}{\|}}{CH}-SnCl_3$ | 81° C | 30 % |
| 5 | mesityl oxide | $CH_3-\overset{\overset{O}{\|\|}}{C}-CH_2-\overset{\overset{CH_3}{\|}}{\underset{\underset{CH_3}{\|}}{C}}-SnCl_3$ | 123° C | 51 % |
| 6 | phorone | $\overset{\overset{CH_3}{\|}}{\underset{\underset{CH_3}{\|}}{C}}=CH-\overset{\overset{O}{\|\|}}{C}-CH_2-\overset{\overset{CH_3}{\|}}{\underset{\underset{CH_3}{\|}}{C}}-SnCl_3$ | 77° C | 42 % based on phorone |
| 7 | crotonic acid | $HOOC-CH_2-\overset{\overset{CH_3}{\|}}{CH}-SnCl_3$ | * | 41 % |

EXAMPLES 8-11

In the following experiments first dry gaseous hydrogen chloride was passed into the solution, followed by gradually adding the activated olefin. The results are summarized in Table B.

Table B

| Example | olefin | product | melting point | yield |
|---|---|---|---|---|
| 8 | methyl vinyl ketone | $CH_3-\overset{\overset{O}{\|\|}}{C}-CH_2-CH_2SnCl_3$ | 70° C | 80 % |
| 9 | acryloyl chloride | $Cl-\overset{\overset{O}{\|\|}}{C}-CH_2-CH_2SnCl_3$ | 42° C | 90,5 % |
| 10 | acrylic acid | $HOOC-CH_2-CH_2SnCl_3$ | * | 74 % |
| 11 | **methyl acrylate | $CH_3-O-\overset{\overset{O}{\|\|}}{C}-CH_2-CH_2SnCl_3$ | 70° C | 98,3 % |

*characterization of the product is difficult because it contains impurities.
**in this example the reaction was carried out in a three-neck flask (3l) with 500 g $SnCl_2$, 800 ml diethyl ether, 153 g HCl gas, and 335 g methyl acrylate.

EXAMPLE 12

The applicability of the organotin compounds according to the invention is demonstrated in this and the next example, in which the product obtained in Example 11 is used as starting material for the preparation of a polyvinyl chloride stabilizer.

In this example, 31.8 g of $$CH_3O-\overset{\overset{O}{\|\|}}{C}-CH_2-CH_2SnCl_3$$

were dissolved in 120 ml of butanol in a three neck flask fitted with stirrer, thermometer and reflux condenser, followed by adding 12 g NaOH dissolved in 100 ml of water and continued stirring for 15 minutes at 40° C.

Subsequently, 62.4 g of isooctyl thioglycollate were added and the temperature raised to 85° C. for a period of 30 minutes. The butanol layer was then separated from the aqueous phase; from the butanol layer the butanol was removed by evaporation to leave 82 g of a colorless liquid (quantitative yield based on tin). After hot-filtration the product was characterized by analysis as $$CH_3O-\overset{\overset{O}{\|\|}}{C}-CH_2-CH_2-Sn(SCH_2COOC_8H_{17})_3 \quad (I)$$

This compound (I) was shown to give heat stability in rigid polyvinyl chloride polymer comparable to that obtained by the commonly used monobutyltin tris-(isooctylthioglycollate).

In addition, compound I was satisfactorily substituted for conventional dibutyltin bis(iso octylthioglycollate) in the production of P.V.C. bottles, at a level of 1%.

EXAMPLE 13

In a similar manner as in the foregoing example 31.2 g of the organotin trichloride, dissolved in 110 ml of butanol, were first treated with a solution of 16 g sodium carbonate in 100 ml of water and then with 62.0 g of lauryl mercaptan.

After separation of the butanol layer and removal of the solvent 82 g of a colorless liquid were obtained in quantitative yield based on tin. The product was characterized as $$CH_3O-\overset{\overset{O}{\|\|}}{C}-CH_2-CH_2-Sn(Sc_{12}H_{25})_3 \quad (II)$$

The performance of this compound (II) was then evaluated against the conventional stabilizer monobutyltin tris(lauryl mercaptide) in a PVC bottle formulation comprising 100 PVC, 1 ester lubricant and 1 stabilizer in parts by weight.

The performance of compound II appeared to be fully comparable to that of the conventional stabilizer.

It is to be understood that other halides can be substituted for the chlorides used in the foregoing examples.

Although the invention is described in detail for the purpose of illustration it is to be understood that such detail is solely for that purpose and that variations can be made therein by those skilled in the art without departing from the spirit and scope of the invention except as it may be limited by the claims.

We claim:

1. A process for the preparation of organotin trihalides which comprises reacting in a polar solvent a
   stannous halide,
   hydrogen halide and
   an olefin of the formula $$\begin{array}{cc} R_1 & R_3 \\ | & | \\ C\!\!=\!\!\!=\!\!C \\ | & | \\ R_2 & R_4 \end{array}$$

where $R_1$, $R_2$, $R_3$ and $R_4$ represent an alkyl group with 1-18 carbon atoms, an oxygen-containing hydrocarbon group or a hydrogen atom, provided that at least one of $R_1$ and $R_2$ contains a carbonyl group adjacent to the olefinic double bond, and thereafter isolating the reaction product with the formula $$\begin{array}{cc} R_1 & R_3 \\ | & | \\ HC\!\!-\!\!-\!\!-\!\!C-SnHal_3 \\ | & | \\ R_2 & R_4 \end{array}$$

from the medium.

2. A process according to claim 1 wherein the reaction is carried out at a temperature in the range of 10° to 30° C.

3. A process according to claim 1 wherein the halides are chlorides.

4. A process according to claim 1 wherein the olefin is selected from the group of acrylic acid, acrylate esters, vinyl alkyl ketones and acryloyl halides.

5. The process of claim 1 wherein at least one of $R_1$, $R_2$, $R_3$ and $R_4$ has a carbonyl radical which is an acid group, an ester group, an aldehyde group, an acid halide group or a ketone group.

* * * * *